United States Patent [19]

Heitz et al.

[11] Patent Number: 4,521,584

[45] Date of Patent: Jun. 4, 1985

[54] PROCESS FOR THE PRODUCTION OF BIFUNCTIONAL POLYPHENYLENE ETHERS

[75] Inventors: Walter Heitz, Kirchhain; Wilhelm Risse, Marburg, both of Fed. Rep. of Germany

[73] Assignee: Bayer Aktiengesellschaft, Leverkusen-Bayerwerk, Fed. Rep. of Germany

[21] Appl. No.: 583,652

[22] Filed: Feb. 27, 1984

[30] Foreign Application Priority Data

Mar. 9, 1983 [DE] Fed. Rep. of Germany ....... 3308421

[51] Int. Cl.$^3$ .............................................. C08G 65/44
[52] U.S. Cl. ................... 528/214; 528/212; 528/215; 528/216; 528/217; 528/218; 528/219
[58] Field of Search ................ 528/212, 214–219

[56] References Cited

U.S. PATENT DOCUMENTS

| 3,133,899 | 5/1964 | Kwiatek et al. | 528/219 |
| 3,272,775 | 9/1966 | McNelis | 528/219 |
| 3,392,147 | 7/1968 | Borman | 528/218 |
| 4,061,617 | 12/1977 | Hay | 528/219 |
| 4,258,175 | 3/1981 | Chen | 528/219 |

FOREIGN PATENT DOCUMENTS

| 99887 | 7/1974 | Japan | 528/212 |
| 71374 | 1/1976 | Japan | 528/219 |
| 103861 | 3/1976 | Japan | 528/219 |

OTHER PUBLICATIONS

Chemical Abstract, vol. 82, 17960d (1975).
Chemical Abstract, vol. 82, 17798g.

*Primary Examiner*—Lester L. Lee
*Attorney, Agent, or Firm*—Connolly and Hutz

[57] ABSTRACT

The invention relates to a new process for the production of polyphenylene oxides.

5 Claims, No Drawings

PROCESS FOR THE PRODUCTION OF BIFUNCTIONAL POLYPHENYLENE ETHERS

This invention relates to a process for the production of bifunctional polyphenylene ethers (polyphenylene oxides).

Polyphenylene ethers (or polyphenylene oxides) and several processes for their production are already known (cf. for example J. Am. Chem. Soc.) 81, 6335 (1959), J. Polym. Sci. 58, 581 (1962), U.S. Pat. Nos. 3,306,879, 3,914,266, 3,956,442 and 3,965,069).

Thus, NL-PS 64 13 958, for example, describes a process for the production of polyphenylene ethers in which polyphenylene ethers which are monofunctional, i.e. contain one OH-group, and additionally contain halogen substituents are reacted with NaOH and KOH to form polyfunctional polyphenylene ethers, i.e. polyphenylene ethers containing several OH-groups.

DE-OS 28 22 856 describes a process for the production of polyphenylene oxides containing two terminal hydroxyl groups. In this process, polyphenylene oxides containing only one hydroxyl group receive another hydroxyl group through the incorporation of quinones.

The present invention relates to a process for the production of bifunctional polyphenylene oxides corresponding to the following formula (I):

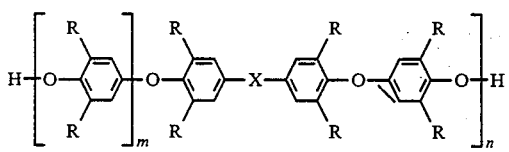

in which R may be the same or different at each position and represents hydrogen, an alkyl radical containing from 1 to 4 carbon atoms, preferably hydrogen or methyl, or an aryl radical containing up to 6 carbon atoms, X represents a group of the formula

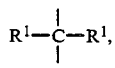

where $R^1$ represents hydrogen or an alkyl radical containing from 1 to 4 carbon atoms

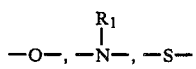

or -SO$_2$-, and m and n are each independently integers of from 1 to 200 and preferably from 5 to 60, characterized in that a mixture of phenols corresponding to the following formulae (II) and (III):

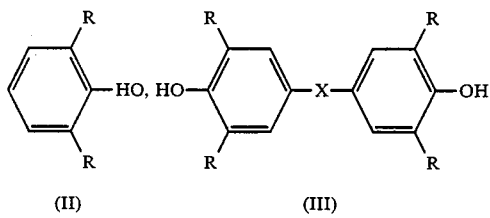

in which R may be the same or different at each position and has the same meaning as in formula (I), and X is as defined above, is reacted with oxygen in an organic solvent in the presents of a catalyst at a temperature of from $-80°$ to $100°$ C. and optionally under elevated pressure.

Suitable organic solvents are aromatic solvents, such as benzene, toluene, ethyl benzene or nitrobenzene; halogentaed solvents, such as carbon tetrachloride, dichloroethane, trichloroethylene, tetrachloroethylene, tetrachloroethane, trichloroethane or chlorobenzene; and pyridines.

Suitable catalysts are metal compounds, for example halides, sulphates and oxides of elements of the 1st and 7th Secondary Group of Mendelejew's Periodic System of Elements (Hofmann Rudorff, Anorganische Chemie, 19th Edition, 1963, page 97, Vieweg Verlag, Braunschweig), such as CuCl, CuBr, Cu$_2$SO$_4$, CuCl$_2$, MnCl$_2$ or Ag$_2$O. In addition there may be used as cocatalysts organic bases, such as pyridine, methyl pyridine, N,N-dimethyl-4-aminopyridine, poly-4-vinyl pyridine, piperidine, morpholine, triethanolamine, and open-chain aliphatic amines, such as n-butylamine, octylamine, dibutylamine, N,N-dimethyl-n-hexylamine, N,N-dimethyl-n-butylamine, triethylamine, (N,N'-ditert.-butyl)-ethylene diamine, 2-aminoethane thiol, 2-mercapto-1-ethanol, 2-mercaptoacetic acid, 1,2-dimercapto-4-methylbenzene, disodium-1,2-dicyanoethylene dithiolate, dimercaptomaleic acid monoamide, Schiff's bases and hydrazones, for example hydrazones of benzoin, polymeric complexes containing bis-(1,2-ethylene dithiolate/Cu II and Cu-II phthalocyanine structures).

The reaction according to the invention is carried out at a temperature in the range of from $-80°$ C. to $100°$ C. and preferably in the range of from $0°$ to $40°$ C. and usually under a pressure of from 0 to 15 bars and preferably under a pressure of from 0 to 5 bars.

From 2 to 400 moles of the phenol (II) are usually used per mole of the phenol (III).

The process according to the invention may be carried out as follows:

The catalyst and cocatalyst are initially introduced in the organic solvent and oxidized with oxygen. The monomer mixture of phenols (II) and (III) is then added in solution in the organic solvent and oxidized with oxygen. This mixture is then left standing at the reaction temperature for a few minutes to several days. The bifunctional polyphenylene oxide is then isolated, for example by precipitation with an alcohol (for example methanol). The reaction product may be analyzed in the usual way (for example by osmometric molecular weight determination, or determination of the phenolic OH-number, for example by titration).

Both symmetrical and asymmetrical bifunctional polyphenylene ethers may be produced by the process according to the invention. According to the invention, symmetrical products are obtained when phenols of formulae (II) and (III) containing the same substitutents are used.

Polymer blocks containing two functional terminal groups and having a high glass transition temperature may be obtained by the process according to the invention. These blocks may be reacted, for example, with acid chlorides, such as phosgene or terephthaloyl-chloride, with diisocyanates, with carbonates and with other polymer blocks to form high molecular weight compounds. Materials produced from these high molecular weight compounds are distinguished by their high dimensional stability under heat .

EXAMPLES

EXAMPLE 1

0.184 g of CuCl (1.86 mMole), 0.332 g of 4-dimethylaminopyridine (2.72 mMoles) and 50 ml of chloroform are introduced into the reaction apparatus which consists of a 500 ml capacity three-necked flask, a KPG-stirrer, a gas inlet pipe and a gas outlet. Oxygen is then introduced into this mixture for 15 minutes at a rate of 15 l/h. A solution of 7 g of 2,6-dimethyl phenol (57.3 mMoles) and 4.1 g of 2,2-bis-(3,5-dimethyl-4-hydroxyphenyl)-propane (14.4 mMoles) in 90 ml of chloroform is introduced at room temperature into this activated copper-amine catalyst solution.

The introduction of oxygen is continued for 2 hours at room temperature and then terminated. The reaction solution is worked up by extraction by shaking twice with 20 ml of a 20% aqueous EDTA trisodium salt solution (EDTA=ethylene diamine tetraacetate), 20 ml of a 15% aqueous HCl-solution, 20 ml of a 10% aqueous $NaHCO_3$-solution and then with distilled water. After the reaction solution thus treated has been dried over $MgSO_4$, the solvent and unreacted 2,6-dimethyl phenol are distilled off respectively at 40° C. in a water jet pump vacuum and at 70° C./0.1 Torr in an oil pump vacuum. 9.6 g of oligomer are obtained (87% of the theoretical, average molecular weight $M_n = 887$, titrated functionality of phenolic hydroxyl groups = 1.89).

EXAMPLE 2

0.8 g of CuCl and 1.7 g of 4-dimethylaminopyridine in 60 ml of chloroform are introduced into a 1 liter reaction vessel, after which oxygen is introduced with stirring for 20 minutes at a rate of 15 l/h. A solution of 20 g of 2,2-bis-(3,5-dimethyl-4-hydroxyphenyl)-propane and 35 g of 2,6-dimethyl phenol in 270 ml of $CHCl_3$ is then added. The introduction of oxygen in a constant stream is continued for another 3 hours at room temperature. The reaction solution is washed twice with 40 ml portions of a 20% aqueous EDTA-trisodium salt solution, a 15% aqueous HCl solution, a 10% aqueous $NaHCO_3$ solution and distilled water.

After drying and removal of the solvent and unreacted monomer by distillation, polyphenylene oxide oligomer is obtained in a yield of 49.7 g (90.3% of the theoretical, average molecular weight $M_n = 395$, titrated functionality of phenolic hydroxyl groups = 1.63).

EXAMPLE 3

0.4 g of CuCl and 1 g of 4-dimethylaminopyridine are introduced with 60 ml of $CHCl_3$ into a 1 liter reaction vessel. Oxygen is passed through this catalyst solution with stirring at a rate of 15 liters per hour. After 20 minutes, a solution of 10.25 g of 2,2-bis-(3,5-dimethyl-4-hydroxyphenyl)-methane (40.0 mMoles) and 30.1 g of 2,6-dimethyl phenol (24.6 mMoles) in 320 ml of chloroform is added at room temperature. The introduction of oxygen is terminated after 3 hours and the reaction solution is worked up in the same way as in Example 2. After the solvent and unreacted 2,6-dimethyl phenol have been distilled off, 36.1 g of oligomer are obtained (91.1% of the theoretical, average molecular weight $M_n$ as determined by vapour pressure osmometry = 518, titrated functionality of the phenolic OH-groups 1.52).

What is claimed is:
1. A process for the production of bifunctional polyphenylene oxides:

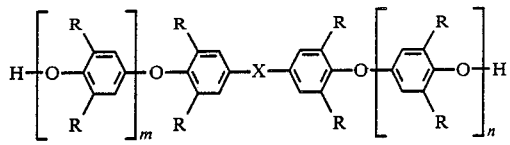

where R is the same or different at each position and is an alkyl moiety containing from 1 to 4 carbon atoms or an aryl moiety containing up to 6 carbon atoms, X is

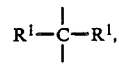

-O-,

-S- or $SO_2$-, where $R^1$ is hydrogen or an alkyl radical containing from 1 to 4 carbon atoms, and m and n are integers of from 1 to 200, comprising,
(1) introducing a metal compound catalyst into an organic solvent and oxidizing the catalyst in the presence of oxygen; then
(2) adding a mixture of phenols,

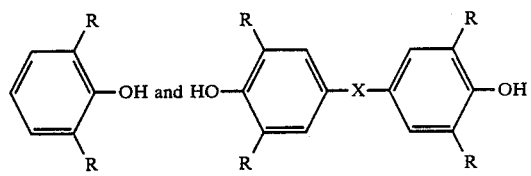

where R is the same or different at each position, and reacting the mixture in the presence of oxygen at a temperature of from −80° C. to 100° C. and at a pressure of 0–15 bar.

2. The process of claim 1 further comprising adding a cocatalyst, where the cocatalyst is an organic base, to the organic solvent and oxidizing the cocatalyst along with the catalyst.

3. The process of claim 1 wherein the catalyst is an halide, sulphate or oxide of a metal of the 1st or 7th Secondary Group of the Periodic System of Elements.

4. The process of claim 1 wherein the catalyst is CuCl, CuBr, $Cu_2SO_4$, $CuCl_2$, Mg $Cl_2$ or $Ag_2O$.

5. The process of claim 2 wherein the cocatalyst is pyridine, methyl pyridine, N,N-dimethyl-4-aminopyridine, poly-4-vinyl pyridine, piperidine, morpholine, triethanolamine, n-butylamine, octylamine, dibutylamine, N,N-dimethyl-n-hexylamine, N,N-dimethyl-n-butylamine, triethylamine, (N,N'-di-tert.-butyl)-ethylene diamine, 2-aminoethane thiol, 2-mercapto-1-ethanol, 2-mercaptoacetic acid, 1,2-dimercapto-4-methylbenzene, disodium-1,2-dicyanoethylene dithiolate, dimercaptomaleic acid monoamide, Schiff's bases or hydrazones.

* * * * *